(12) United States Patent
Lanois et al.

(10) Patent No.: US 9,526,494 B1
(45) Date of Patent: Dec. 27, 2016

(54) BONE ANCHOR DELIVERY SYSTEM DEVICE AND METHOD

(71) Applicant: Valeris Medical, LLC, Marietta, GA (US)

(72) Inventors: Daniel Brian Lanois, Atlanta, GA (US); C. Grey Friend, Roswell, GA (US)

(73) Assignee: Valeris Medical, LLC, Marietta, GA (US)

( * ) Notice: Subject to any disclaimer, the term of this patent is extended or adjusted under 35 U.S.C. 154(b) by 0 days.

(21) Appl. No.: 14/974,697

(22) Filed: Dec. 18, 2015

(51) Int. Cl.
    *A61B 17/04* (2006.01)
    *A61B 17/3205* (2006.01)
    *A61B 17/00* (2006.01)

(52) U.S. Cl.
CPC ..... *A61B 17/0401* (2013.01); *A61B 17/32053* (2013.01); *A61B 2017/00367* (2013.01); *A61B 2017/044* (2013.01); *A61B 2017/0409* (2013.01); *A61B 2017/0425* (2013.01)

(58) Field of Classification Search
CPC ............... A61B 17/1401; A61B 2017/0409; A61B 2017/0414; A61B 2017/042; A61B 2017/0438; A61B 2017/0445; A61B 2017/0446; A61B 2017/0451; A61B 2017/0459; A61B 2017/0456; A61B 2017/8655; A61F 2/0811; A61F 2002/0823; A61F 2002/0835
USPC ........................................ 606/232; 623/13.14
See application file for complete search history.

(56) References Cited

U.S. PATENT DOCUMENTS

| | | |
|---|---|---|
| 5,480,403 A | 1/1996 | Lee et al. |
| 5,649,963 A | 7/1997 | McDevitt |
| 5,935,129 A | 8/1999 | McDevitt et al. |
| 5,957,953 A | 9/1999 | Dipoto et al. |
| 5,968,078 A | 10/1999 | Grotz |
| 6,544,281 B2 | 4/2003 | Elattrache et al. |
| 6,660,023 B2 | 12/2003 | McDevitt et al. |
| 7,329,272 B2 | 2/2008 | Burkhart et al. |
| 7,993,369 B2 | 8/2011 | Dreyfuss et al. |
| 8,133,258 B2 | 3/2012 | Foerster et al. |
| 8,430,909 B2 | 4/2013 | Dreyfuss et al. |
| 8,613,756 B2 | 12/2013 | Lizardi et al. |
| 8,986,345 B2 | 3/2015 | Denham |
| 9,078,646 B2 | 7/2015 | Lizardi et al. |

(Continued)

FOREIGN PATENT DOCUMENTS

EP      0574707      12/1993

*Primary Examiner* — Kathleen Holwerda
*Assistant Examiner* — Socrates L Boutsikaris
(74) *Attorney, Agent, or Firm* — David L. King (57) ABSTRACT

A bone anchor delivery system device has a retractable punch driver assembly and a bone anchor assembly for attachment onto the punch driver assembly. The punch driver assembly has a retractable punch shaft and a guide for receiving the retractable punch shaft. The punch shaft is linearly movable relative to the guide and the punch shaft having an extended length with bone penetrating tip at a first end. The bone anchor assembly has a bone anchor having a hollow body, a punch, an intermediate lock. The intermediate lock is stowed at a distal end portion inside the hollow body of the bone anchor near a proximal end of the punch and when moved toward a proximal end of the bone anchor the intermediate lock moves inside and expands the hollow body diametrically increasing in size to secure the bone anchor to a bone opening.

23 Claims, 13 Drawing Sheets

(56) References Cited

U.S. PATENT DOCUMENTS

| | | | |
|---|---|---|---|
| 2003/0088250 A1* | 5/2003 | Colleran | A61B 17/0401 606/232 |
| 2006/0235413 A1* | 10/2006 | Denham | A61B 17/0401 606/232 |
| 2009/0299386 A1* | 12/2009 | Meridew | A61F 2/0805 606/151 |
| 2009/0312794 A1 | 12/2009 | Nason et al. | |
| 2011/0004258 A1* | 1/2011 | Stone | A61B 17/0401 606/329 |
| 2011/0112550 A1 | 5/2011 | Heaven et al. | |
| 2013/0103083 A1 | 4/2013 | Baird | |
| 2013/0131723 A1 | 5/2013 | Snell et al. | |
| 2013/0267998 A1 | 10/2013 | Vijay et al. | |
| 2013/0268001 A1 | 10/2013 | Catanese et al. | |
| 2014/0046369 A1 | 2/2014 | Heaven et al. | |
| 2014/0222072 A1 | 8/2014 | Gerber et al. | |
| 2014/0257381 A1* | 9/2014 | Palese | A61B 17/0401 606/232 |

\* cited by examiner

BONE ANCHOR DELIVERY SYSTEM DEVICE AND METHOD

TECHNICAL FIELD

The present invention relates to methods and instruments for fixation of sutures and tissue to bone, more particularly to a bone anchor system for securing sutures for attachment of soft tissue like ligament and cartilage to bone.

BACKGROUND OF THE INVENTION

The use of bone screw anchors to hold sutures is a widely accepted practice in shoulder or knee repair and fixation of soft tissue such as ligaments, cartilage and tendons to bone. Ideally the suture anchor is easy to install and provides a solid reliable way to fix the sutures to the bone. The bone has a hard outer cortical shell with a softer underlying region of cancellous bone tissue. The anchor must hold sutures after thousands of repetitive motions tensioning and relaxation until the ligament or tendon repair has time to heal and secure itself to the bone and muscle tissue.

Older style bone anchors had an external eyelet to allow the sutures to be fed through after the screw was driven into the bone. This left the eyelet exposed in the soft muscle tissue.

Later versions of bone anchors have the sutures inserted inside the screw tip well inside the bone. This allows the screw outer end to stay flush with the cortical bone outer surface. The sutures can pass inside in some hollow screws from the tip to the outer surface. Others have the sutures held at the tip end and are exterior held between the anchor screw threads and the bone. In some suture anchor systems there is a self-driving feature that has a stainless steel punch with a steel tip that can be malleted into the bone. This design leaves the tip end trapped in the bone opening meaning the patient has a small steel tip in his shoulder or knee.

Ideally the procedure should insure the bone anchor is easily installed leaving no punch tip fragments in the body and more particularly avoiding having steel tips or metal fragments left in the bone.

The present invention provides a threaded bone anchor that is easy to install wherein the sutures are held without leaving metal fragments or metal tips and, furthermore, this is accomplished with a unique insertion tool and anchor screw assembly to make the procedure simple and convenient to use.

SUMMARY OF THE INVENTION

A bone anchor delivery system device has a retractable punch driver assembly and a bone anchor assembly for attachment onto the punch driver assembly. The punch driver assembly has a retractable punch shaft and a guide for receiving the retractable punch shaft. The punch shaft is linearly movable relative to the guide and the punch shaft having an extended length with bone penetrating tip at a first end. The bone anchor assembly has a bone anchor having a hollow body, a punch, an intermediate lock. The intermediate lock is stowed at a distal end portion inside the hollow body of the bone anchor near a proximal end of the punch and when moved toward a proximal end of the bone anchor the intermediate lock moves inside and expands the hollow body diametrically increasing in size to secure the bone anchor to a bone opening.

In one embodiment, the retractable punch shaft has a reduced diameter end for receiving a bone anchor assembly with a bone anchor and a releasable punch extending from the tip toward a shoulder stop on the guide. The releasable punch has a hollow opening for receiving the reduced diameter end and bone penetration tip at the first end profiled to be complimentary to the tip and an opposite second end for abutting the bone anchor mounted on the punch shaft. The releasable punch has a plurality of openings for threading one or more sutures wherein the releasable punch openings are one or more pairs of slots sized to receive a one or more sutures. At least one slot in each pair has the opening configured to be a non-slip opening to receive the suture in the direction of suture entry, but frictionally resist suture pull back in the opposite direction.

The non-slip opening can be a narrowing slit wide at one surface and narrow at an opposite surface of the punch. The non-slip opening can have pluralities of serrations along edges of the slot to hold the suture from pulling back.

DEFINITIONS

As used in this specification, the singular forms "a," "an" and "the" include plural referents unless the context clearly dictates otherwise. Thus, for example, the term "a material" is intended to mean one or more materials, or a combination thereof.

BRIEF DESCRIPTION OF THE DRAWINGS

The invention will be described by way of example and with reference to the accompanying drawings in which.

DETAILED DESCRIPTION OF THE INVENTION

Figure 1:
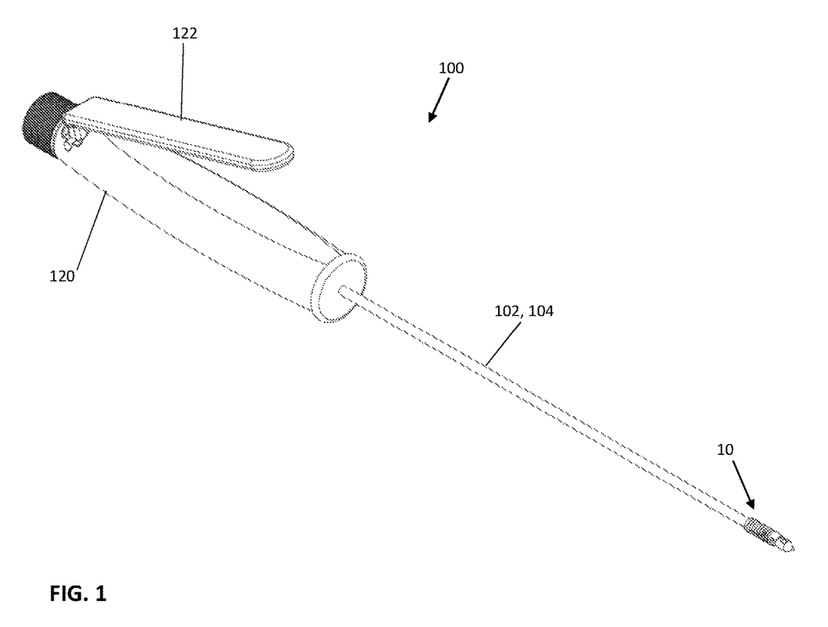
FIG. 1 shows a perspective view of the bone anchor delivery system device of the present invention.

With reference to FIG. 1, the bone anchor delivery system 100 is illustrated. The bone anchor delivery system 100 has a handle 120 with a trigger mechanism 122. Attached to the handle 120 is shown a retractable punch 104 inside a punch guide 102. At a distal end of the punch shaft 104 is shown a bone anchor assembly 10.

Figure 2:
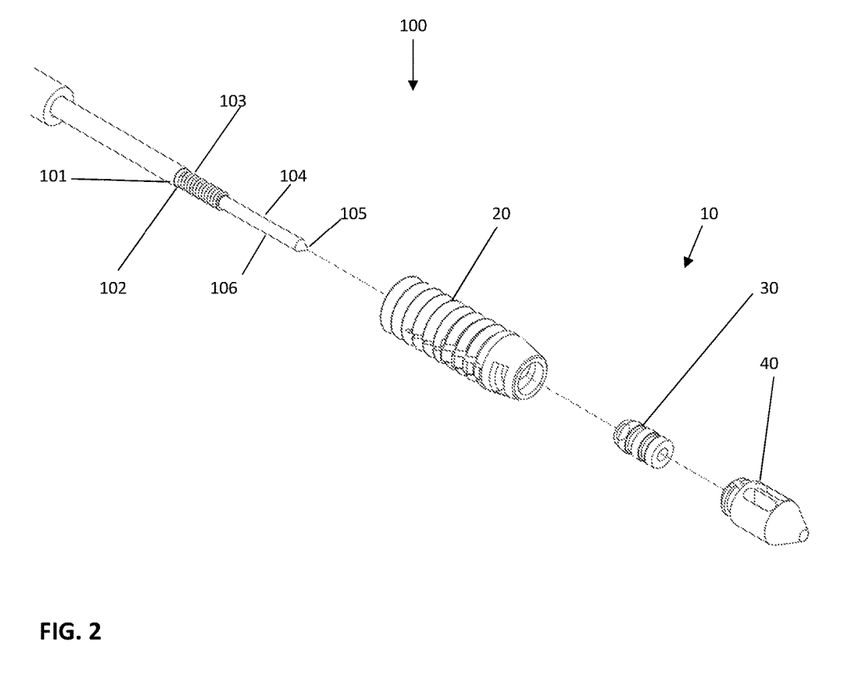
FIG. 2 is a partial exploded view showing the bone anchor, the intermediate lock and the punch removed from the punch tip of the bone anchor delivery system.
Figure 3:
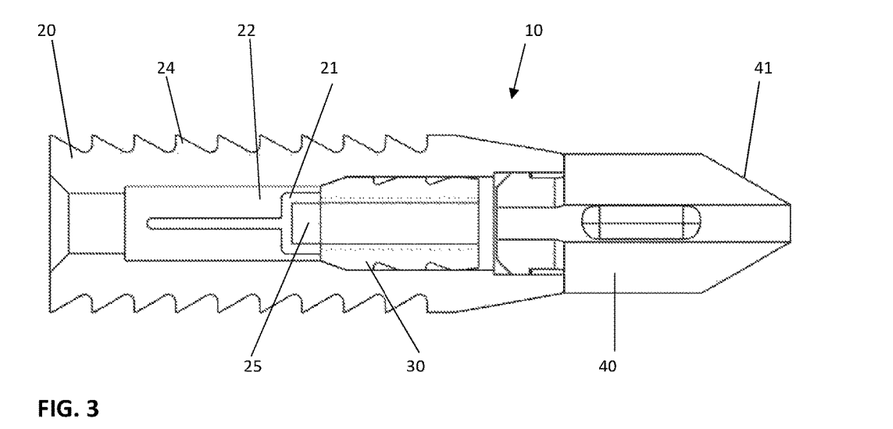
FIG. 3 is a cross sectional view of the bone anchor assembly showing the punch, the intermediate lock and the threaded bone anchor.
Figure 4:
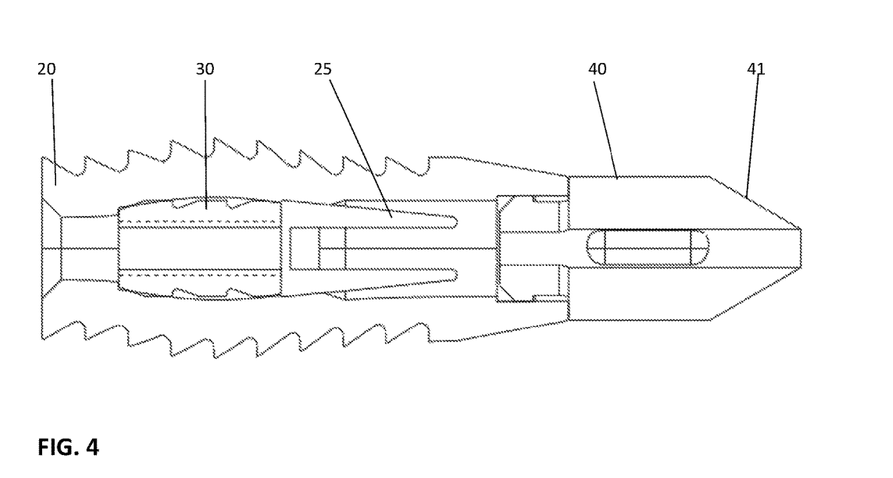
FIG. 4 is a cross sectional view showing the intermediate lock moved into the locked position inside the bone anchor assembly.

As shown in FIG. 2, the bone anchor assembly 10 is formed of three components, a first bone anchor 20, an intermediate lock 30 and a punch 40. On assembly, the three components appear as shown in FIG. 3, depicting the bone anchor assembly 10. The bone anchor 20 is at the proximal end of the bone anchor assembly 10. The bone anchor 20 has threads or flutes 24 on the exterior surface of the hollow bone anchor 20. The punch 40 is at a distal end of the bone anchor assembly 10. Inside the bone anchor 20 hollow body is the intermediate lock 30 shown positioned inside a cavity 22 wherein the assembly 10 is shown in the non-expanded and unlocked position with the lock 30 closer to the distal end of the bone anchor 20. The bone anchor 20 has a plurality of slots 21 which allow the bone anchor 20 to expand diametrically when the intermediate lock 30 is moved proximally into the position as shown in FIG. 4. The intermediate lock 30, when moved towards the proximal end will stop when it abuts an end. On each side of the bone anchor 20 are the slots 21 which have a fork shape with an upper center slot 21 and two lower slots 21 branched and spaced apart to form a locking tab 25 between the lower slots 21. The bone anchor 20 has a pair of these tabs 25, one tab 25 on each side. When the lock 30 passes and expands the diameter of the bone anchor 20, the tab 25 mechanically is moved inward on each side to block the base of the lock 30 as shown in FIG. 4. Bone anchor 20, as shown, has both distal and proximal ends formed as continuous rings. All diametrical expansion occurs between the ends along slots 21. The lock 30 has a diameter larger than an unexpanded diameter of the interior cavity 22. As such, as it moves toward the proximal end, the outer threads or flutes 24 of the bone anchor 20 are pushed outwardly to firmly engage bone 2 when implanted. The lock 30 can be ribbed circumferentially to prevent slippage. The entire assembly 10 as shown in FIG. 1, when installed on the retractable punch 104 abuts against the guide 102. As illustrated, the bone anchor assembly 10 when placed onto the retractable punch 104 and guide sleeve 102 has the bone anchor 20 positioned against shoulder stop 101 of the guide 102. The punch shaft 104 having threads 103 that are internally threaded into the intermediate lock 30. The retractable punch shaft 104 extends further and passes a reduced diameter end 106, shown in FIG. 2, through all three components through apertures in the anchor 20, lock 30 and punch 40 such that the tip 105 of the retractable punch shaft 104 can be used to penetrate the bone when assembling the bone anchor assembly 10. The punch 40 has a complimentary conical shaped frustoconical end 41. All three bone anchor components 20, 30, 40 can be made preferably of a synthetic material, plastic in particular PEEK (polyether ether ketone) material can be used so that on insertion, the bone anchor assembly 10 can be inserted firmly into bone without leaving any metal fragments or components.

Figure 5:
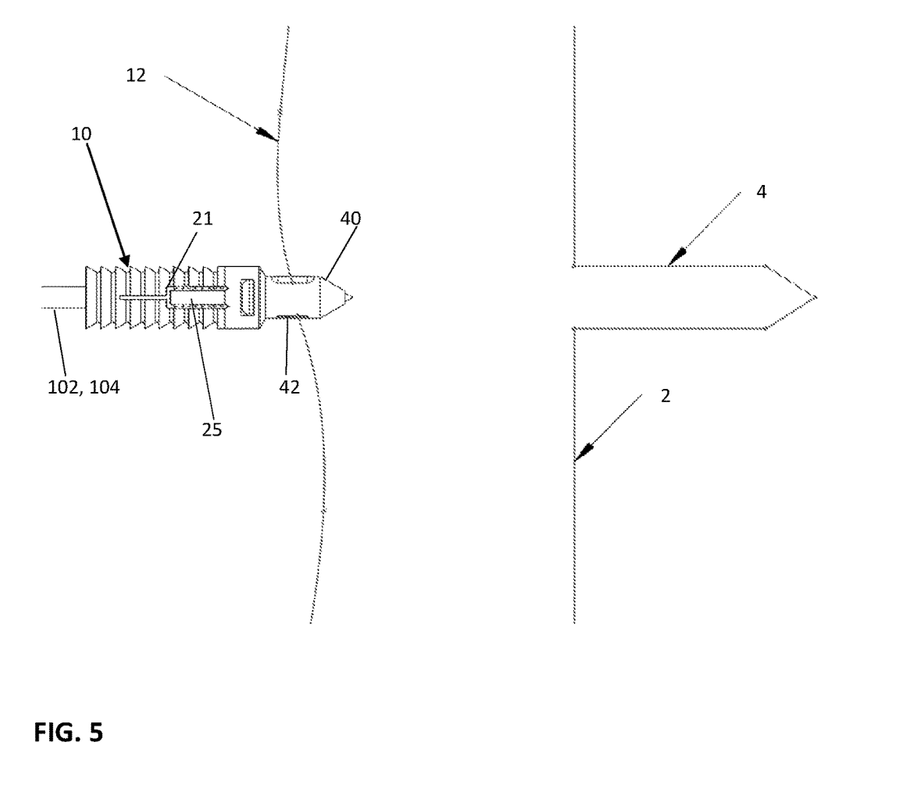
FIG. 5 shows a bone predrilled with the bone anchor assembly on the punch with sutures passed through the openings.
Figure 6:
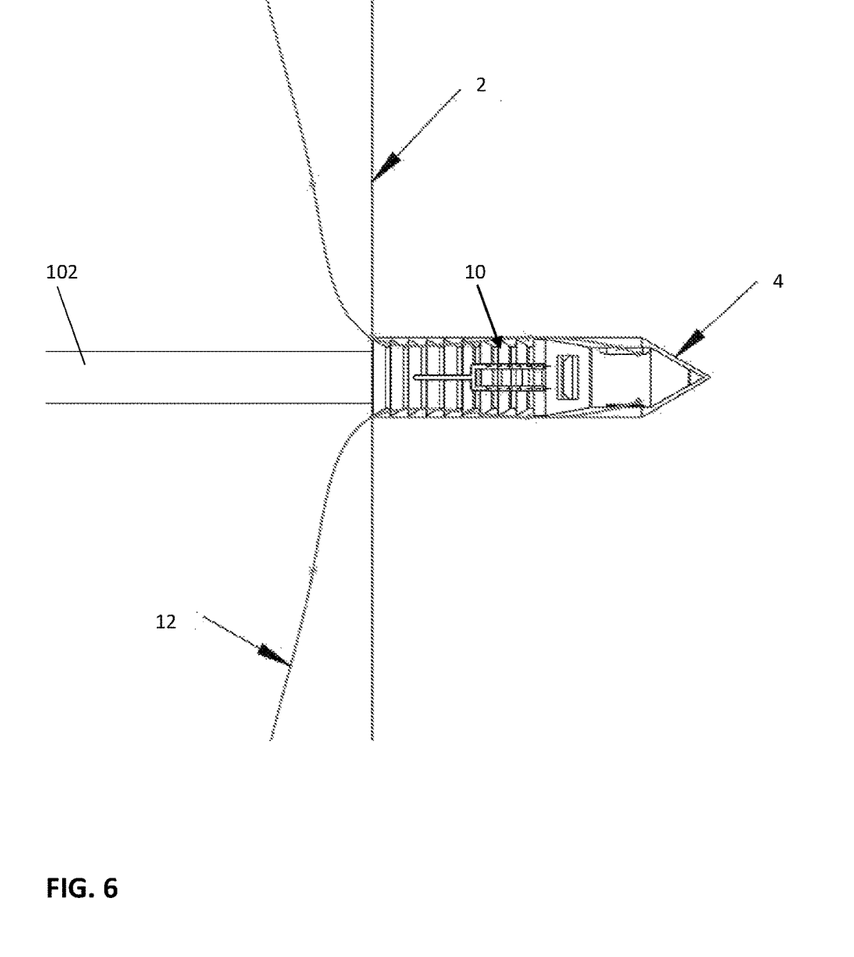
FIG. 6 shows the bone anchor assembly with sutures delivered into the drilled bone tunnel.
Figure 7:
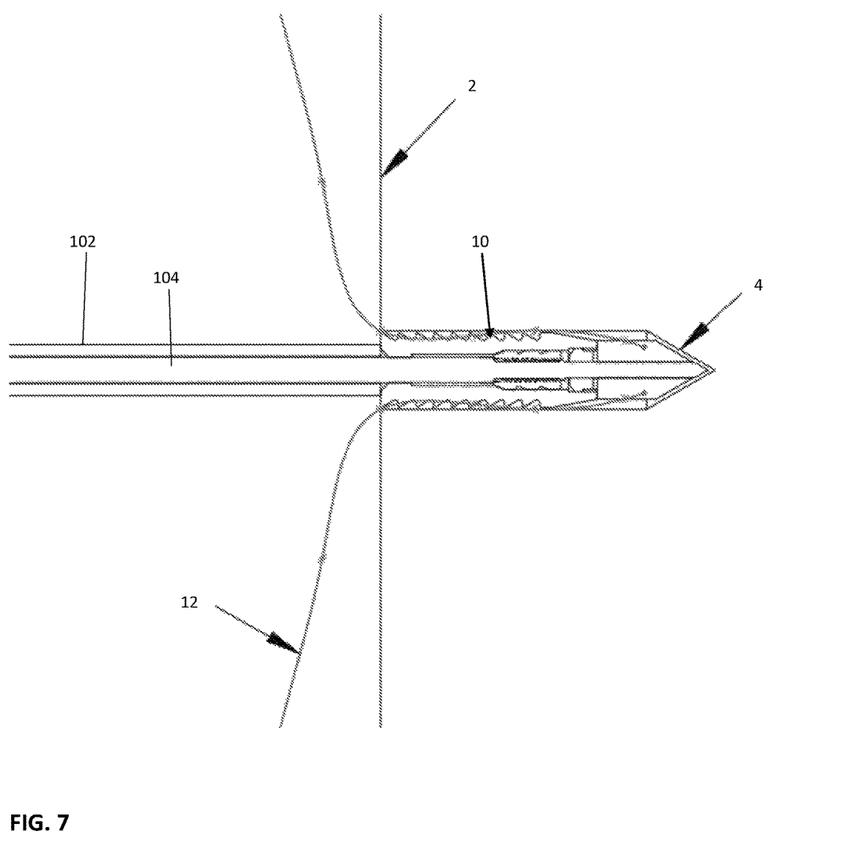
FIG. 7 is a cross sectional view of FIG. 6.
Figure 8:
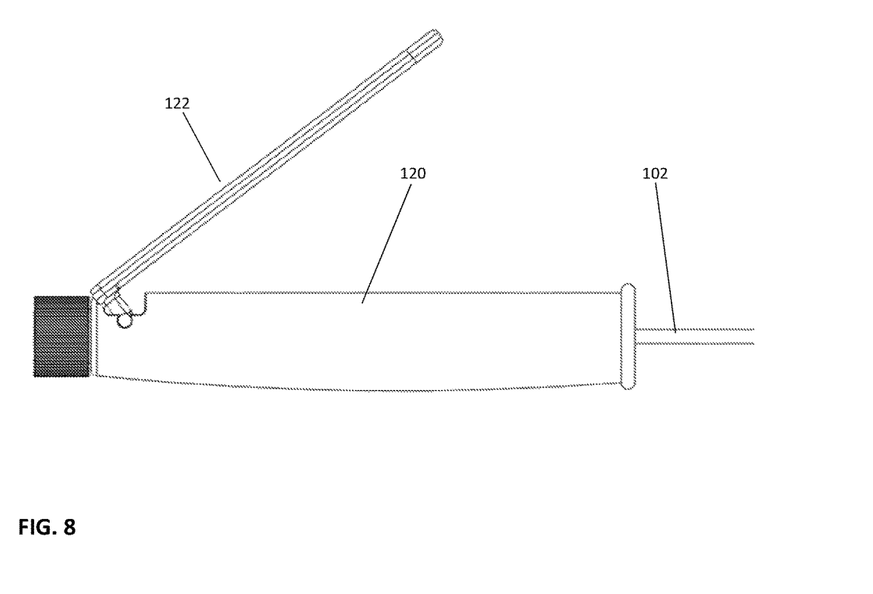
FIG. 8 shows a portion of the driver assembly handle with the trigger in the upward position.
Figure 9:
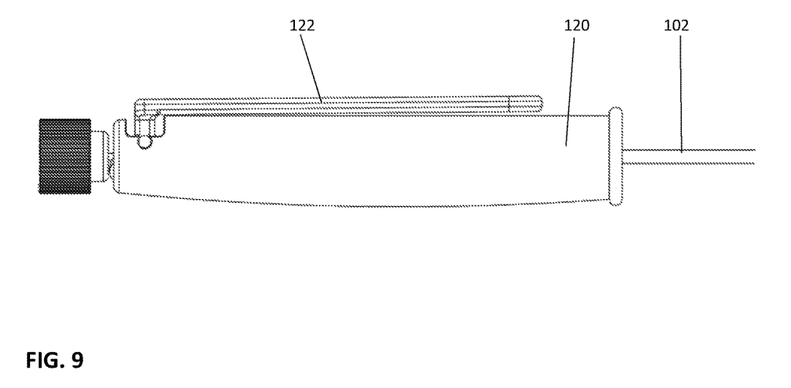
FIG. 9 shows the trigger in the retracted down position.
Figure 10:
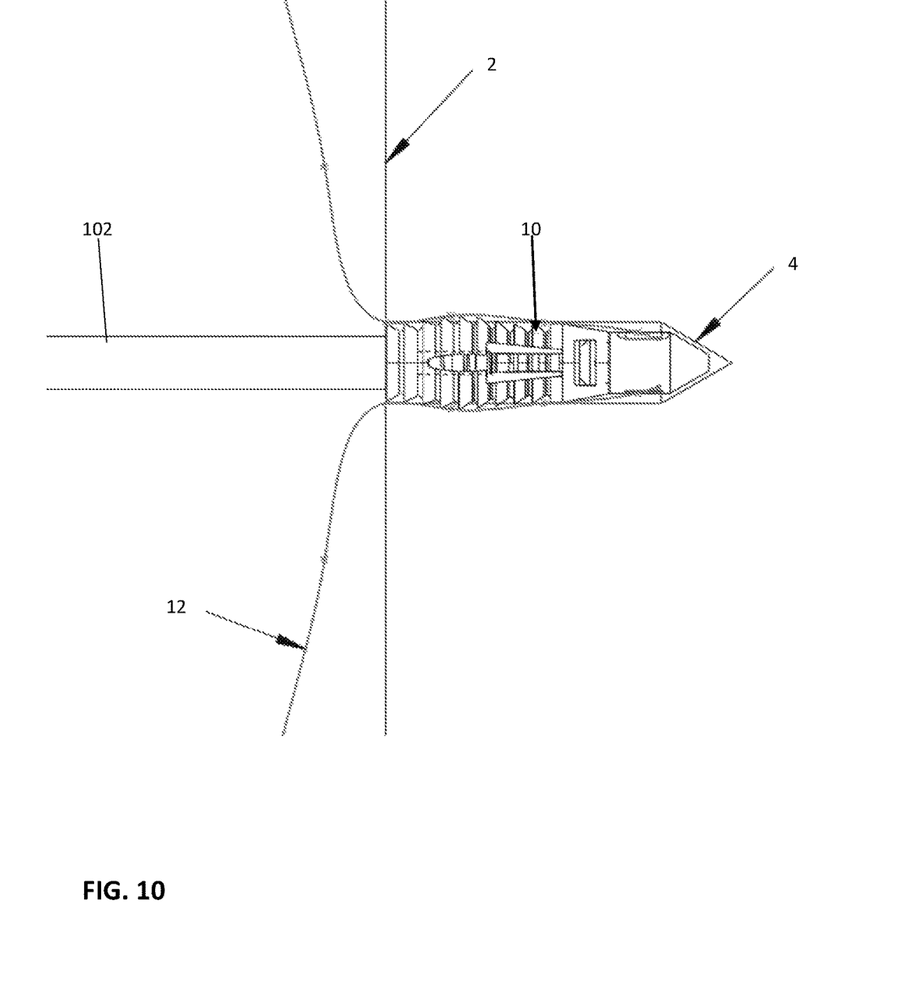
FIG. 10 shows the expanded bone anchor in the bone tunnel with the sutures shown exposed above the bone and the intermediate lock in the locked position.
Figure 11:
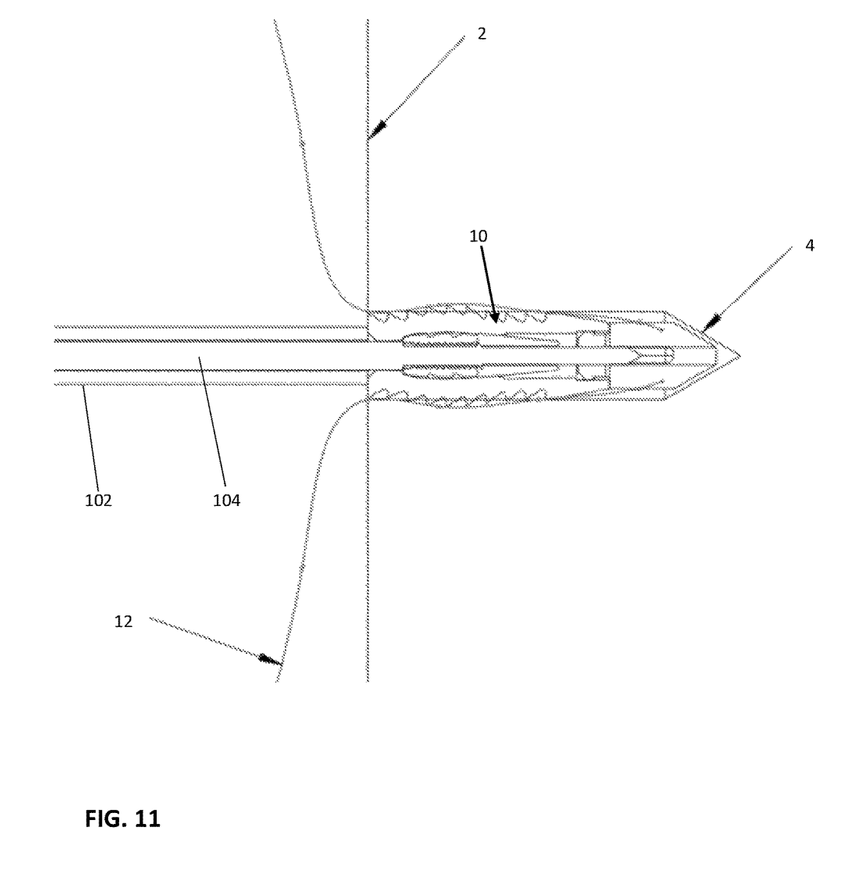
FIG. 11 is a cross sectional view of FIG. 10.
Figure 12:
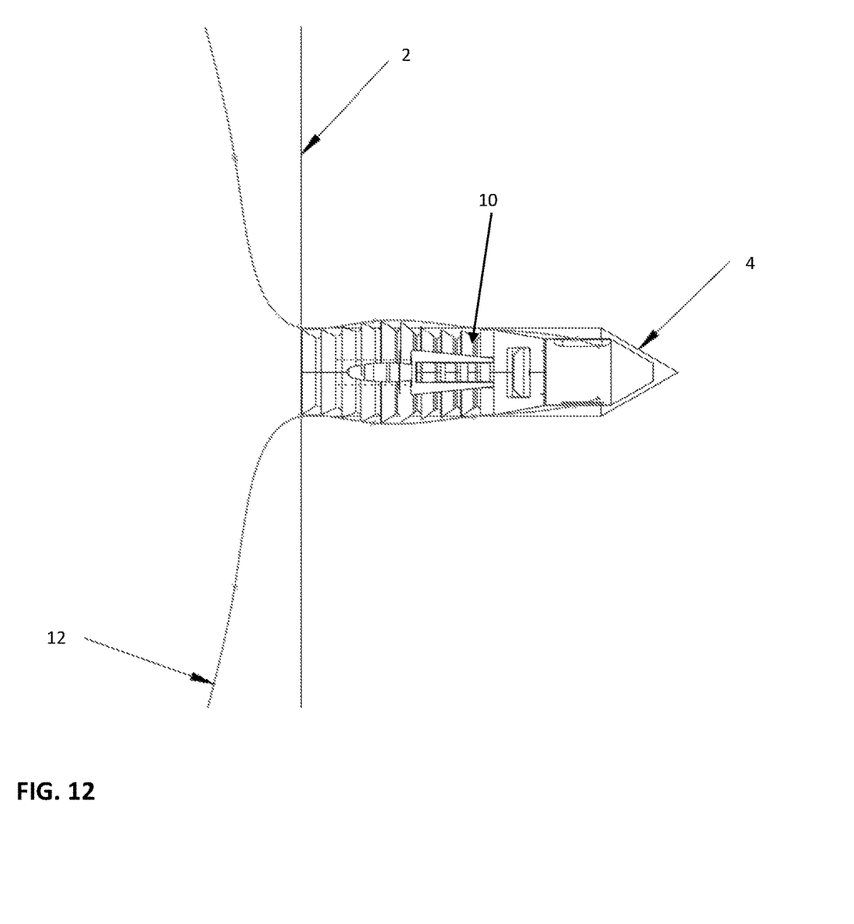
FIG. 12 shows the punch removed from the bone anchor assembly.

With reference to FIG. 5, the bone anchor assembly 10 is shown fixed to the retractable punch shaft 104 and guide 102 with a suture 12 passing through slotted openings 42 in the punch 40. A pre-drilled bone tunnel 4 is shown drilled into the bone 2 and the retractable punch 104 and the bone anchor assembly 10 are shown in FIG. 6 inserted inside the pre-drilled bone tunnel 4. On assembly, the bone anchor assembly 10 fits loosely within the bone tunnel 4 and the sutures can be pulled in the illustrated embodiment in either direction to tighten or tension the sutures 12 as desired. Once the sutures 12 are tightened, a trigger mechanism 122 on the handle 120 can be activated. When the trigger mechanism 122, illustrated in FIG. 9, is activated, the retractable punch 104 is retracted and the intermediate lock 30 is pulled into the expanded locked position as illustrated. In the expanded position, the flutes or threads 24 on the bone anchor 20 are expanded due to the slot 21 configuration along the longitudinal length of the bone anchor 20. As the intermediate lock 30 pulls towards the proximal direction towards the opening in the bone 2, the lock 30 seats itself inside the proximal end of the bone anchor 20 and expands the bone anchor 20 so the threads or flutes 24 are tightly engaged against the bone 2. When this occurs, the sutures 12 are in the locked position and cannot be moved. At this point, with the handle 120 in the retracted position, the inner shaft or retractable punch 104 can be unscrewed from the lock 30. This completes the assembly as illustrated in FIG. 12, with the delivery device completely disengaged from the assembled bone anchor assembly 10.

Figure 13:
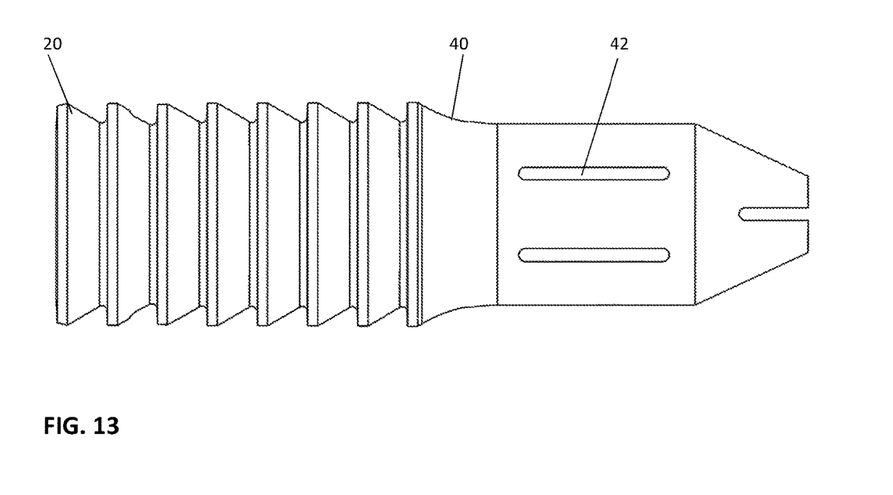
FIG. 13 is an exemplary alternative embodiment of the punch of the present invention.
Figure 13A:
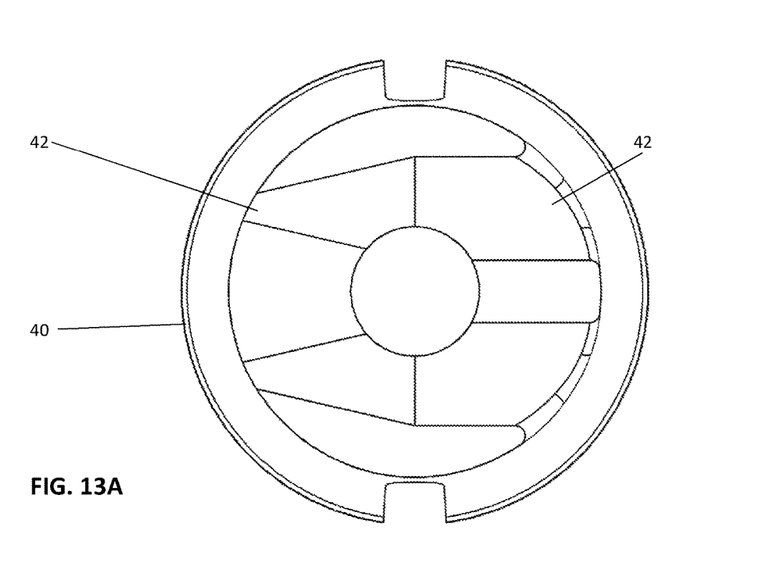
FIG. 13A is a cross sectional view of the alternative embodiment punch of FIG. 13.
Figure 14:
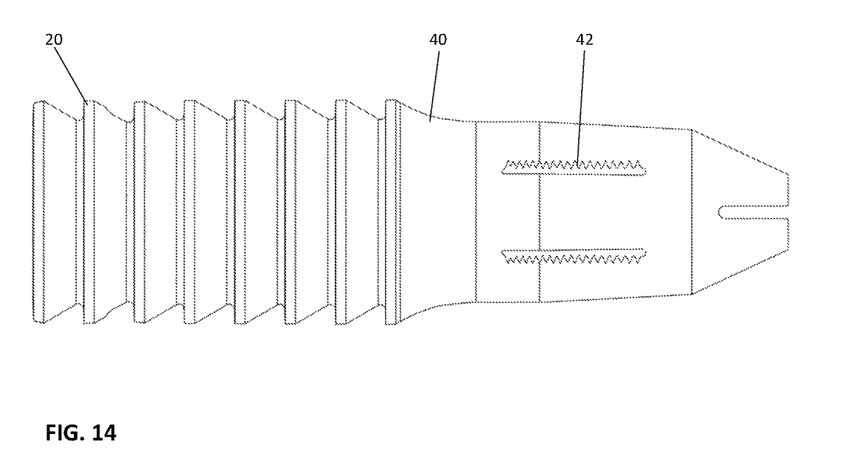
FIG. 14 is a second embodiment alternative punch.
Figure 15:
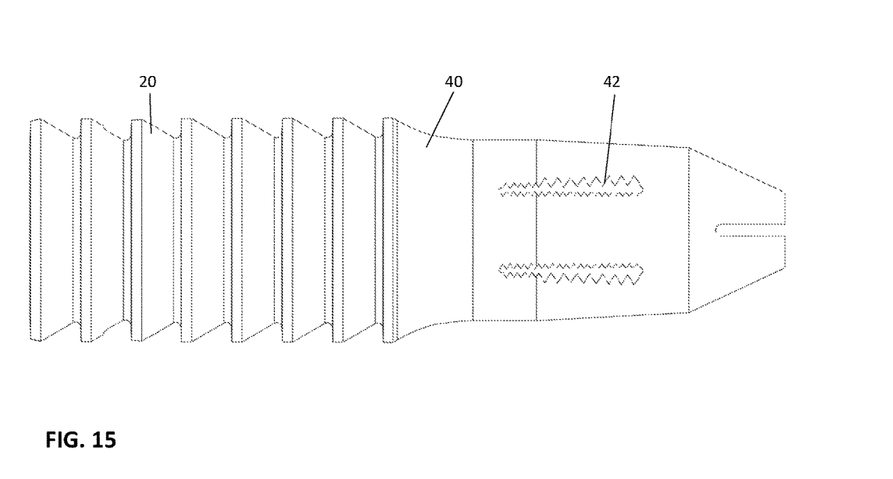
FIG. 15 is a third embodiment alternative punch.

An improved version of the punch 40 is illustrated in the alternative embodiments of FIGS. 13-15. In these embodiments, as shown in FIG. 13A, the openings 42 in the punch 40 can be configured in such a fashion that the sutures 12 will enter wide side ports or openings and pass across the punch 40 to narrow slotted openings 42. These narrow openings 42 create a one-way feature. Narrow on one side and wide on the other, the suture 12 will slide from the wide to the narrow side and will be unable to slide backwards from the narrow side to the wide side. This has been determined to be quite beneficial in that when the sutures 12 are free to slide back and forth within the slotted openings, it is difficult to hold a device and both ends of the suture to maintain a proper amount of tension. However, with the present invention having one-way slotted openings 42, it is possible for the suture 12 attached to a ligament to be tightened to a proper tension and this tension will be held in the punch 40 without slipping backwards. Therefore, the surgeon only has to deal with one end of the suture 12 to create a tensioning while the other end of the suture 12 is properly tensioned. Therefore, on locking the device into position, the portion of the suture 12 pre-attached to soft tissue can be held at a proper tension while the surgeon only has to deal with the free end of the suture 12 which may or may not require tensioning. This frees up the surgeon and provides a more accurate way of tensioning a pre-attached ligament or soft tissue.

In FIG. 14, the punch 40 is illustrated with serrations on one side. These serrations can bite into the suture 12 and also provide a fixation. Similarly, in FIG. 15, these serrations can be made on both sides of the slot 42. In such case the slotted openings 42 as noted are wider at the distal end and narrow at the proximal end. This allows the suture 12 to be drawn upward to the proximal end and pinched into place. In either event, the suture 12 will not be free to slide within the punch 40 using these alternatives. However, it creates a beneficial improvement over punches where the slotted opening 42 allows free movement of the suture 12 in both directions.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone anchor delivery system comprising:
a retractable punch driver assembly, the retractable punch driver assembly having a retractable punch shaft and a guide for receiving the retractable punch shaft, the retractable punch shaft being linearly movable relative to the guide and the retractable punch shaft having an extended length and a bone penetrating tip at a first end thereof;
a bone anchor assembly for attachment onto the retractable punch driver assembly, the bone anchor assembly having a bone anchor having a hollow body, a punch, and an intermediate lock, wherein the entire bone anchor assembly, when installed on the retractable punch shaft extends from the bone penetrating tip of the retractable punch shaft and abuts against the guide; and
wherein the intermediate lock is stowed at a distal end portion inside the hollow body of the bone anchor near a proximal end of the punch and when the intermediate lock is moved toward a proximal end of the bone anchor the intermediate lock moves inside and expands the hollow body diametrically to secure the bone anchor to a bone opening, wherein the bone anchor has a plurality of slots which allow the bone anchor to expand diametrically when the intermediate lock is moved proximally into a locked position, the slots each having a fork shape with an upper center slot and two lower slots branched apart to form a locking tab between the two lower slots, wherein the locking tabs move inward as the intermediate lock is moved proximally, and as the intermediate lock passes the locking tabs, the locking tabs block the intermediate lock as the intermediate lock abuts the proximal end of the bone anchor.

2. The bone anchor delivery system of claim 1 further comprises a handle and a trigger mechanism, said trigger mechanism attached to the handle, the trigger mechanism also attached to the retractable punch shaft at a proximal end of the retractable punch shaft, wherein when the trigger mechanism is closed, the retractable punch shaft retracts.

3. The bone anchor delivery system of claim 1 wherein the bone anchor has threads or flutes on an exterior surface of the bone anchor.

4. The bone anchor delivery system of claim 1 wherein the intermediate lock has a diameter larger than an unexpanded diameter of an interior cavity of the bone anchor and as the intermediate lock moves toward the proximal end of the bone anchor, outer threads or flutes of the bone anchor are pushed outwardly to firmly engage bone when implanted.

5. The bone anchor delivery system of claim 1 wherein the retractable punch shaft has threads that are capable of being internally threaded into threads on the intermediate lock.

6. The bone anchor delivery system of claim 1 wherein the bone penetrating tip of the retractable punch shaft is capable of being extended through apertures in the bone anchor, intermediate lock and punch, to penetrate bone and initiate formation of the bone opening when implanting the bone anchor assembly.

7. The bone anchor delivery system of claim 1 wherein the punch has a complimentary conical shaped frustoconical end to the bone penetrating tip.

8. The bone anchor delivery system of claim 1 wherein the bone anchor assembly is made of a synthetic or plastic material.

9. The bone anchor delivery system of claim 8 wherein the synthetic or plastic material is PEEK (polyether ether ketone).

10. A bone anchor delivery system comprising:
a retractable punch driver assembly, the retractable punch driver assembly having a retractable punch shaft and a guide for receiving the retractable punch shaft, the retractable punch shaft being linearly movable relative to the guide and the retractable punch shaft having an extended length and a bone penetrating tip at a first end thereof; and
wherein the retractable punch shaft has a reduced diameter end extending from the bone penetrating tip toward a shoulder stop, the retractable punch shaft receiving a bone anchor assembly, the bone anchor assembly having a bone anchor, an intermediate lock, and a releasable punch, wherein the bone anchor has a plurality of slots which allow the bone anchor to expand diametrically when the intermediate lock is moved proximally into a locked position, the slots each having a fork shape with an upper center slot and two lower slots branched apart to form a locking tab between the two lower slots, wherein the locking tabs move inward as the intermediate lock is moved proximally, and as the intermediate lock passes the locking tabs, the locking tabs block the intermediate lock as the intermediate lock abuts a proximal end of the bone anchor, the releasable punch having a hollow opening for receiving the reduced diameter end and having the bone penetration tip extending therethrough, the releasable punch at a first end is profiled to be complimentary to the bone penetrating tip and has an opposite second end that abuts the bone anchor when mounted on the retractable punch shaft, the releasable punch has a plurality of openings for threading one or more sutures wherein the plurality of openings of the releasable punch are one or more pairs of slots sized to receive a plurality of sutures, at least one slot in each pair is configured to be a non-slip opening to receive a suture in a direction of suture entry, but frictionally resist suture pull back in an opposite direction.

11. The bone anchor delivery system of claim 10 further comprises a handle and a trigger mechanism, said trigger mechanism attached to the handle, the trigger mechanism also attached to the retractable punch shaft at a proximal end of the retractable punch shaft, wherein when the trigger mechanism is closed, the retractable punch shaft retracts.

12. The bone anchor delivery system of claim 10 wherein the bone anchor has threads or flutes on an exterior surface of the bone anchor.

13. The bone anchor delivery system of claim 10 wherein the intermediate lock has a diameter larger than an unexpanded diameter of an interior cavity of the bone anchor and as the intermediate lock moves toward the proximal end of the bone anchor, outer threads or flutes of the bone anchor are pushed outwardly to firmly engage bone when implanted.

14. The bone anchor delivery system of claim 10 wherein the entire bone anchor assembly, when installed on the retractable punch shaft, abuts against the guide.

15. The bone anchor delivery system of claim 10 wherein the retractable punch shaft has threads that are capable of being internally threaded into threads on the intermediate lock.

16. The bone anchor delivery system of claim 10 wherein the bone penetrating tip of the retractable punch shaft is capable of being extended through apertures in the bone anchor, the intermediate lock and releasable punch to penetrate bone when implanting the bone anchor assembly.

17. The bone anchor delivery system of claim 10 wherein the releasable punch has a complimentary conical shaped frustoconical end to the bone penetrating tip.

18. The bone anchor delivery system of claim 10 wherein the bone anchor assembly is made of a synthetic or plastic material.

19. The bone anchor delivery system of claim 18 wherein the synthetic or plastic material is PEEK (polyether ether ketone).

20. The bone anchor delivery system of claim 10 wherein the non-slip opening is a narrowing slit wide at one surface and narrow at an opposite surface of the releasable punch.

21. The bone anchor delivery system of claim 20 wherein the non-slip opening has pluralities of serrations along edges of the slot to hold the suture from pulling back.

22. The bone anchor delivery system of claim 10 wherein the reduced diameter end of the retractable punch shaft and the releasable punch have a snap lock feature to hold the releasable punch, the snap lock feature allows for rotational movement of the releasable punch relative to the retractable punch shaft.

23. A bone anchor assembly comprising:
a bone anchor having a hollow body;
a punch;
an intermediate lock; and
wherein the intermediate lock is stowed at a distal end portion inside the hollow body of the bone anchor near a proximal end of the punch and when moved toward a proximal end of the bone anchor the intermediate lock moves inside and expands the hollow body diametrically to secure the bone anchor to a bone opening, wherein the bone anchor has a plurality of slots which allow the bone anchor to expand diametrically when the intermediate lock is moved proximally into a locked position, the slots each having a fork shape with an upper center slot and two lower slots branched apart to form a locking tab between the two lower slots, wherein the locking tabs move inward as the intermediate lock is moved proximally and as the intermediate lock passes the locking tabs, the locking tabs block the intermediate lock as the intermediate lock abuts the proximal end of the bone anchor.

\* \* \* \* \*